US009603669B2

United States Patent
Govari et al.

(10) Patent No.: US 9,603,669 B2
(45) Date of Patent: *Mar. 28, 2017

(54) PRESSURE SENSING FOR A MULTI-ARM CATHETER

(71) Applicant: BIOSENSE WEBSTER (ISRAEL) LTD., Yokneam (IL)

(72) Inventors: Assaf Govari, Haifa (IL); Andres Claudio Altmann, Haifa (IL); Orit Kolin-Schwartz, Moshav Manoff (IL)

(73) Assignee: Biosense Webster (Israel) Ltd. (IL)

( * ) Notice: Subject to any disclaimer, the term of this patent is extended or adjusted under 35 U.S.C. 154(b) by 8 days.

This patent is subject to a terminal disclaimer.

(21) Appl. No.: 14/822,057

(22) Filed: Aug. 10, 2015

(65) Prior Publication Data

US 2015/0342700 A1 Dec. 3, 2015

Related U.S. Application Data

(63) Continuation of application No. 13/542,090, filed on Jul. 5, 2012, now Pat. No. 9,101,396, which is a (Continued)

(51) Int. Cl.
*A61B 5/103* (2006.01)
*A61B 5/117* (2016.01)
(Continued)

(52) U.S. Cl.
CPC .......... *A61B 19/5244* (2013.01); *A61B 34/20* (2016.02); *A61B 90/10* (2016.02);
(Continued)

(58) Field of Classification Search
CPC ....................................................... A61B 5/00
(Continued)

(56) References Cited

U.S. PATENT DOCUMENTS 3,841,150 A 10/1974 Pearson
3,971,364 A 7/1976 Fletcher et al.
(Continued)

FOREIGN PATENT DOCUMENTS

DE 19750441 A 6/1999
EP 928601 A1 7/1999
(Continued)

OTHER PUBLICATIONS

Biter, William J. et al., "Magnetic Wire Strain Sensor", 33rd International Sampe Technical Conference, Nov. 5-8, 2001, vol. 33, pp. 12-23, Seattle, WA.

(Continued)

*Primary Examiner* — Rene Towa
*Assistant Examiner* — May Abouelela
(74) *Attorney, Agent, or Firm* — Vincent J. Serrao (57) ABSTRACT

A method for operating a medical probe includes pressing a distal end of the medical probe, which includes one or more arms that extend diagonally outward from a central shaft and have respective position transducers coupled thereto, against an intra-body surface, so as to cause the arms to exert pressure on the surface and bend with respect to the central shaft in response to the pressure. Positions of the respective position transducers coupled to the arms are measured, and the pressure exerted by the arms is estimated responsively to the measured positions.

20 Claims, 3 Drawing Sheets

Related U.S. Application Data continuation of application No. 12/827,254, filed on Jun. 30, 2010, now Pat. No. 8,226,580.

(51) Int. Cl.
*A61B 19/00* (2006.01)
*A61M 25/01* (2006.01)
*A61M 25/00* (2006.01)
*A61B 17/00* (2006.01)
*A61B 18/14* (2006.01)
*A61B 18/00* (2006.01)

(52) U.S. Cl.
CPC .... *A61M 25/0068* (2013.01); *A61M 25/0082* (2013.01); *A61M 25/0127* (2013.01); *A61B 17/0057* (2013.01); *A61B 17/00234* (2013.01); *A61B 18/1492* (2013.01); *A61B 2017/00053* (2013.01); *A61B 2018/00345* (2013.01); *A61B 2018/00577* (2013.01); *A61B 2034/2051* (2016.02); *A61B 2034/2059* (2016.02); *A61B 2090/064* (2016.02); *A61B 2090/065* (2016.02); *A61M 2025/0002* (2013.01); *A61M 2025/0166* (2013.01)

(58) Field of Classification Search
USPC .......................................... 600/587, 595, 424
See application file for complete search history.

(56) References Cited

U.S. PATENT DOCUMENTS

| | | |
|---|---|---|
| 4,566,465 A * | 1/1986 | Arhan ............... A61B 5/1076 600/587 |
| 4,764,114 A | 8/1988 | Jeffcoat et al. |
| 4,856,993 A | 8/1989 | Maness et al. |
| 4,930,494 A | 6/1990 | Takehana et al. |
| 5,263,493 A | 11/1993 | Avitall |
| 5,368,564 A | 11/1994 | Savage |
| 5,391,199 A | 2/1995 | Ben-Haim |
| 5,452,719 A * | 9/1995 | Eisman ............... A61N 1/0512 600/373 |
| 5,462,527 A | 10/1995 | Stevens-Wright et al. |
| 5,487,757 A | 1/1996 | Truckai et al. |
| 5,499,542 A | 3/1996 | Morlan |
| 5,542,434 A | 8/1996 | Imran et al. |
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A | 6/1998 | Abela et al. |
| 5,814,098 A * | 9/1998 | Hinnenkamp ........ A61F 2/2496 33/512 |
| 5,826,576 A | 10/1998 | West |
| 5,833,605 A * | 11/1998 | Shah ..................... G01B 7/13 33/512 |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,865,801 A * | 2/1999 | Houser ................. A61B 5/036 600/488 |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,036,654 A * | 3/2000 | Quinn .................. A61B 5/028 600/339 |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 | 7/2001 | Osadchy et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,398,738 B1 | 6/2002 | Millar |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Schwartz et al. |
| 6,835,173 B2 | 12/2004 | Couvillon, Jr. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,003,342 B2 * | 2/2006 | Plaza .................. A61B 5/0422 600/374 |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,911,315 B2 | 3/2011 | Bradley |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,357,152 B2 | 1/2013 | Govari et al. |
| 8,374,819 B2 | 2/2013 | Govari et al. |
| 8,535,308 B2 | 9/2013 | Govari et al. |
| 8,900,229 B2 | 12/2014 | Govari et al. |
| 8,926,528 B2 | 1/2015 | Govari et al. |
| 9,033,916 B2 | 5/2015 | Schultz |
| 9,265,913 B2 * | 2/2016 | Fallin ................... A61M 1/008 |
| 2001/0047129 A1 | 11/2001 | Hall et al. |
| 2001/0047133 A1 | 11/2001 | Gilboa et al. |

(56) References Cited

U.S. PATENT DOCUMENTS

| | | |
|---|---|---|
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0068931 A1 | 6/2002 | Wong et al. |
| 2002/0087089 A1 | 7/2002 | Ben-Haim |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0043649 A1* | 2/2005 | Urie ................. A61B 5/037 600/561 |
| 2005/0080429 A1 | 4/2005 | Freyman et al. |
| 2005/0096590 A1 | 5/2005 | Gullickson et al. |
| 2005/0148903 A1* | 7/2005 | Diamantopoulos ...... A61B 5/01 600/587 |
| 2005/0171569 A1* | 8/2005 | Girard ............. A61B 17/00234 606/193 |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1* | 3/2006 | Omata ................. A61B 5/103 600/587 |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0241366 A1* | 10/2006 | Falwell ............... A61B 5/0422 600/374 |
| 2006/0247618 A1 | 11/2006 | Kaplan et al. |
| 2006/0276703 A1* | 12/2006 | Fuimaono ........... A61B 5/0422 600/374 |
| 2007/0021742 A1 | 1/2007 | Viswanathan |
| 2007/0060832 A1 | 3/2007 | Levin |
| 2007/0060847 A1 | 3/2007 | Leo et al. |
| 2007/0083193 A1* | 4/2007 | Werneth ............. A61B 5/0422 606/41 |
| 2007/0100332 A1 | 5/2007 | Paul et al. |
| 2007/0106114 A1 | 5/2007 | Sugimoto et al. |
| 2007/0106165 A1 | 5/2007 | Tulkki |
| 2007/0142749 A1 | 6/2007 | Khatib et al. |
| 2007/0151116 A1* | 7/2007 | Malandain .......... A61B 1/3135 33/512 |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167804 A1 | 7/2007 | Park |
| 2007/0167818 A1 | 7/2007 | Osborn et al. |
| 2007/0167819 A1 | 7/2007 | Osborn, III et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0233044 A1 | 10/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0161796 A1 | 7/2008 | Cao et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsumura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0062642 A1* | 3/2009 | Hauck .................. A61B 5/0053 600/429 |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306521 A1* | 12/2009 | Ermakov ............. A61B 5/0075 600/477 |
| 2009/0306650 A1 | 12/2009 | Govari et al. |
| 2009/0318798 A1* | 12/2009 | Singh .................... A61B 1/012 600/424 |
| 2010/0036285 A1* | 2/2010 | Govari .............. A61B 19/5244 600/587 |
| 2010/0063478 A1* | 3/2010 | Selkee .................. A61B 5/042 604/524 |
| 2010/0069921 A1 | 3/2010 | Miller et al. |
| 2010/0121138 A1 | 5/2010 | Goldenberg et al. |
| 2010/0121214 A1* | 5/2010 | Giftakis ................ A61B 5/031 600/544 |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0222668 A1* | 9/2010 | Dalke ................. A61K 51/0491 600/424 |
| 2010/0262001 A1* | 10/2010 | Morris .................. A61M 5/158 600/424 |
| 2010/0274239 A1 | 10/2010 | Paul et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0152880 A1 | 6/2011 | Alvarez et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |

(56) References Cited

U.S. PATENT DOCUMENTS

| | | |
|---|---|---|
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 8266486 | 10/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| JP | 2010-036040 A | 2/2010 |
| WO | WO 94/17856 A1 | 8/1994 |
| WO | WO 95/10326 A | 4/1995 |
| WO | WO 96/05768 A | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/043884 A1 | 4/2006 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Biter, William J. et al., "Magnetic Wire for Monitoring Strain in Composites", Sensors, Jun. 2001, www.sensormag.com, pp. 110-114.
Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.
Instron Marketing Brochure, "Medical Device Testing Systems", Instron 2007 http://web.archive.org/web/20080318092822/http://www.instron.com.tr/wa/library/streamfile.aspx?doc=1678&downland=true.
Instron, "Series 3300 Load Frames, Reference Manual Equipment", Instron, pp. 1-5 and 1-10, 2004.
Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).
Okumura, M.D. Yasuo et al. "A Systematic Analysis of In Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.
Peirs, J. et al., "Design of an Optical Force Sensor for Force Feedback during Minimally Invasive Robotic Surgery", Eurosensors XVII, 2003, pp. 1063-1066, http:/_/mech.kuleuven.be/micro/pub/medic/Paper_Eurosensors_2003_MIS_sensor_extended.pdf.
Partial European Search Report mailed on Sep. 18, 2009 from related European Patent Application No. 08253265.6.
Partial European Search Report mailed on Dec. 7, 2009 from related European Patent Application No. 09251502.2.
European Search Report mailed on Mar. 8, 2010 from related European Patent Application No. 09252143.4.
Partial European Search Report mailed on Mar. 29, 2010 from related European Patent Application No. 09252879.3.
Partial European Search Report mailed on Apr. 1, 2010 from related European Patent Application No. 09252721.7.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Sep. 23, 2011 from related European Patent Application No. 11169251.3.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

* cited by examiner

PRESSURE SENSING FOR A MULTI-ARM CATHETER

CROSS REFERENCE TO RELATED APPLICATIONS

This application is a continuation of U.S. patent application Ser. No. 13/542,090, filed Jul. 5, 2012, which is a continuation of U.S. patent application Ser. No. 12/827,254, filed Jun. 30, 2010, now U.S. Pat. No. 8,226,580, the entire contents of both of which are incorporated herein by reference.

FIELD OF THE INVENTION

The present invention relates generally to invasive probes, and specifically to determining pressure exerted by a multi-arm catheter on a surface.

BACKGROUND OF THE INVENTION

A wide range of medical procedures involve placing objects, such as sensors, tubes, catheters, dispensing devices and implants, within the body. Position sensing systems have been developed for tracking such objects. Magnetic position sensing is one of the methods known in the art. In magnetic position sensing, magnetic field generators are typically placed at known positions external to the patient. One or more magnetic field sensors within the distal end of a probe generate electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

In addition to catheters with a single distal tip discussed supra, U.S. Pat. No. 6,574,492, whose disclosure is incorporated herein by reference, discusses a catheter with a tuft of multiple resilient arms (also referred to as lobes) extending from the distal end of the catheter. Each of the distal arms has a position sensor and one or more electrodes. There is also an additional position sensor in the distal end of the catheter, located at the base of the tuft.

When placing a probe within the body, it may be desirable to have the distal tip(s) of the probe in direct contact with body tissue. The contact can be verified, for example, by measuring the contact pressure between the distal tip(s) and the body tissue. U.S. Patent Application Publications 2007/0100332, 2009/0093806 and 2009/0138007, whose disclosures are incorporated herein by reference, describe methods of sensing contact pressure between the distal tip of a catheter and tissue in a body cavity using a force sensor embedded in the catheter. The distal tip of the catheter is coupled to the distal end of the catheter insertion tube by a resilient member, such as a spring, which deforms in response to force exerted on the distal tip when it presses against endocardial tissue. A magnetic position sensor within the catheter senses the deflection (location and orientation) of the distal tip relative to the distal end of the insertion tube. Movement of the distal tip relative to the insertion tube is indicative of deformation of the resilient member, and thus gives an indication of the pressure.

SUMMARY OF THE INVENTION

An embodiment of the present invention that is described herein provides a method for operating a medical probe, including:

pressing a distal end of the medical probe, which includes one or more arms that extend diagonally outward from a central shaft and have respective position transducers coupled thereto, against an intra-body surface, so as to cause the arms to exert pressure on the surface and bend with respect to the central shaft in response to the pressure;

measuring positions of the respective position transducers coupled to the arms; and estimating the pressure exerted by the arms responsively to the measured positions.

In some embodiments, the medical probe includes a catheter. In an embodiment, estimating the pressure includes verifying a physical contact between the arms and the surface. In a disclosed embodiment, estimating the pressure includes identifying that a given arm makes a physical contact with the surface by detecting, using the measured positions, a change in a curvature of the given arm. In another embodiment, measuring the positions includes applying one or more magnetic fields in a vicinity of the probe, receiving from the position transducers respective signals, which are generated by the position transducers responsively to the magnetic fields and are indicative of the respective positions of the position transducers, and calculating the positions based on the received signals.

In some embodiments, estimating the pressure includes calculating at least one distance between at least one respective pair of the position transducers, and estimating the pressure responsively to the distance. In another embodiment, estimating the pressure includes calculating at least one angle between at least one respective pair of the arms, and estimating the pressure responsively to the angle. In yet another embodiment, estimating the pressure includes calculating at least one angle between the central shaft and at least one of the arms, respectively, and estimating the pressure responsively to the angle. In still another embodiment, estimating the pressure includes applying to the measured positions a pre-calibrated relation between the pressure and the positions.

In an embodiment, measuring the positions includes measuring a position of an additional position transducer that is coupled to the central shaft, and estimating the pressure includes assessing the pressure responsively to the measured position of the additional position transducer. Estimating the pressure may include calculating at least one distance between the additional position transducer and a respective at least one of the position transducers, and estimating the pressure responsively to the distance. In an embodiment, estimating the pressure includes calculating at least one angle between the central shaft and a respective at least one of the arms, and estimating the pressure responsively to the angle.

In some embodiments, the method includes displaying an image of the arms and the surface to an operator, and selecting a graphical feature using which the arms are presented in the image responsively to the estimated pressure. In an embodiment, the method includes selectively enabling sensing of signals by one or more electrodes coupled to at least one of the arms responsively to the estimated pressure.

There is additionally provided, in accordance with an embodiment of the present invention, including:

a medical probe, having a distal end including one or more arms that extend diagonally outward from a central shaft and have respective position transducers coupled thereto, the arms configured to press against an intra-body surface so as to exert pressure on the surface and bend with respect to the central shaft in response to the pressure; and a processor, which is configured to measure positions of the respective position transducers coupled to the arms, and to estimate the pressure exerted by the arms responsively to the measured positions.

There is also provided, in accordance with an embodiment of the present invention, a computer software product, operated in conjunction with a medical probe that includes one or more arms that extend diagonally outward from a central shaft and have respective position transducers coupled thereto, the product including a computer-readable medium, in which program instructions are stored, which instructions, when read by a computer, cause the computer to measure positions of the respective position transducers coupled to the arms, and to estimate the pressure exerted by the arms responsively to the measured positions.

The present invention will be more fully understood from the following detailed description of the embodiments thereof, taken together with the drawings in which:

DETAILED DESCRIPTION OF EMBODIMENTS

Overview

Various diagnostic and therapeutic procedures, such as intracardiac electrical mapping or cardiac ablation, use an invasive probe whose distal tip is fitted with at least one electrode. The electrode is typically operated when the probe is pressed against intra-body tissue. In these procedures, it is usually important to maintain sufficient contact pressure between the probe and the tissue in question. On the other hand, excessive pressure can have undesired effects on the procedure, and in extreme cases even cause physical damage to the tissue.

Embodiments of the present invention provide methods and systems for measuring the pressure that a multi-arm probe (e.g., a catheter) exerts on tissue in a body cavity. In some embodiments, the distal end of a medical probe includes a central shaft and multiple arms that extend diagonally outward from the central shaft. Each arm is fitted with a position transducer. During a medical procedure, the distal end of the catheter is pressed against an intra-body surface, so that the arms exert pressure on the surface. As a result of the pressure, the arms bend with respect to the central shaft. The positions of the position transducers in the arms are measured, and the contact pressure between the arms and the surface is estimated based on the measured positions of the arms.

In some embodiments, an additional position transducer is fitted in the distal end of the central shaft, in addition to the position transducers fitted in the multiple arms. The positions of the different position transducers are measured, including the additional position transducer in the central shaft, and the contact pressure is estimated based on the position measurements.

Although the embodiments described herein refer mainly to multi-arm probes, some of the disclosed techniques can also be used in a probe having a single arm fitted with a position transducer. In some embodiments, the magnitude of the contact pressure is estimated based on the measured positions of the arms. In alternative embodiments, the measured positions of the arms are used to verify physical contact between the arms and the surface, without necessarily measuring the pressure magnitude.

In some embodiments, the dependence of the measured positions on the pressure may be calibrated in advance. Coefficients calculated during a calibration procedure can be stored as a calibration matrix in a non-volatile memory that is coupled to the catheter. Then, when the catheter is inside a body cavity such as a heart, the probe measurements and the calibration coefficients may be used to verify that the electrodes are in contact with the heart wall, and/or that the pressure between the electrodes and the heart wall is in the proper range for ablation and/or sensing.

System Description

Figure 1:
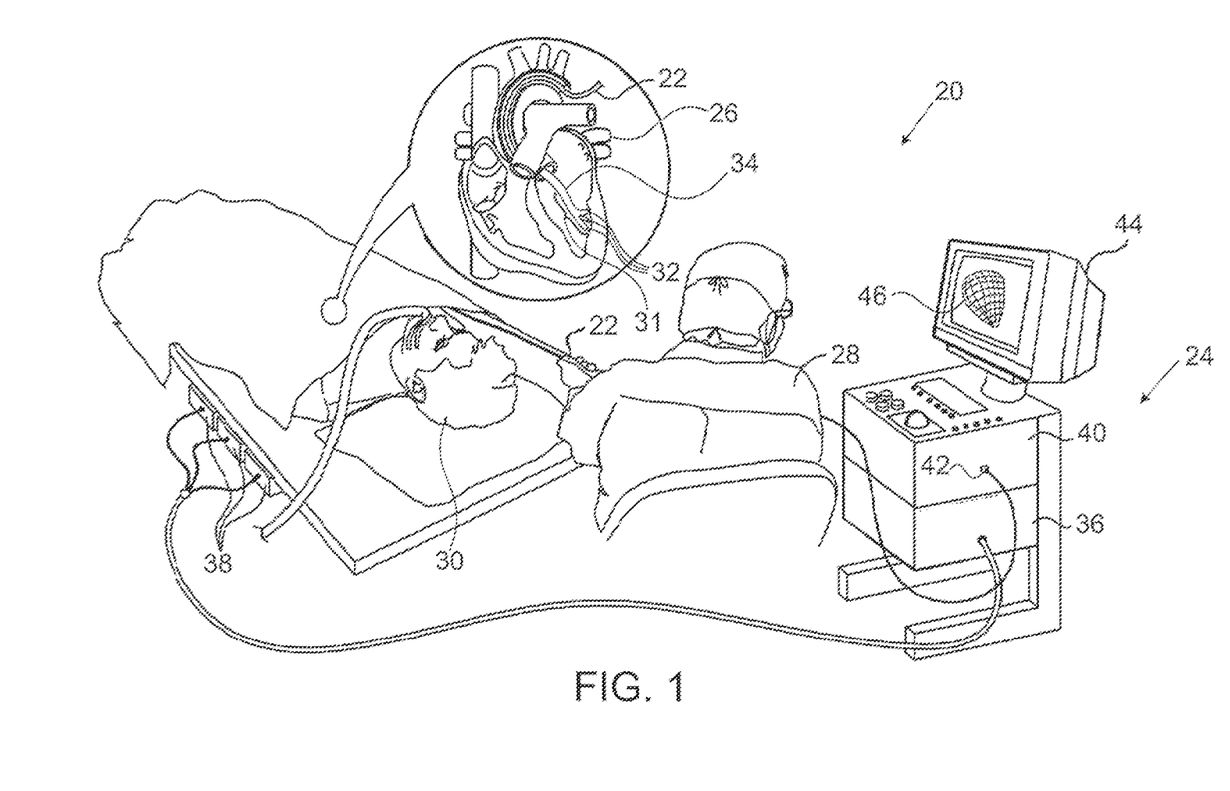
FIG. 1 is a schematic pictorial illustration of a medical system that uses a multi-arm catheter, in accordance with an embodiment of the present invention.

FIG. 1 is an illustration of a medical system 20 that uses a multi-arm catheter, which is constructed and operative in accordance with a disclosed embodiment of the invention. System 20 may be based, for example, on the CARTO™ system, produced by Biosense Webster Inc. (Diamond Bar, Calif.). System 20 comprises a multi-arm probe 22, such as a catheter, and a control console 24. In the embodiment described hereinbelow, it is assumed that probe 22 is used for diagnostic or therapeutic treatment, such as mapping electrical potentials in a heart 26 or performing ablation of heart tissue. Alternatively, probe 22 may be used, mutatis mutandis, for other therapeutic and/or diagnostic purposes in the heart or in other body organs.

An operator 28, such as a cardiologist, inserts multi-arm probe 22 through the vascular system of a patient 30 so that a distal end 31 of probe 22 enters a chamber of the patient's heart 26. Operator 28 advances probe 22 so that the distal end, comprising a plurality of arms 32 extending from a central shaft 34, engages endocardial tissue at a desired location or locations. Probe 22 is typically connected by a suitable connector at its proximal end to console 24.

Console 24 uses magnetic position sensing to determine position coordinates of central shaft 34 and arms 32 inside heart 26. To determine the position coordinates, a driver circuit 36 in console 24 drives field generators 38 to generate magnetic fields within the body of patient 30. Typically, field generators 38 comprise coils, which are placed below the patient's torso at known positions external to patient 30. These coils generate magnetic fields in a predefined working volume that contains heart 26. Magnetic field transducers that are coupled to arms 32 of probe 22, and in some embodiments also to shaft 34, generate electrical signals in response to these magnetic fields. (The distal end of probe 22, arms 32, shaft 34 and the different position transducers are shown in detail in FIG. 2 below.) A signal processor 40 in console 24 processes the electrical signals in order to determine the position coordinates of arms 32 and possibly central shaft 34, typically including both location and orientation coordinates.

Processor 40 typically comprises a general-purpose computer, with suitable front end and interface circuits for receiving signals from probe 22 and controlling the other components of console 24. Processor 40 may be programmed in software to carry out the functions that are described herein. The software may be downloaded to console 24 in electronic form, over a network, for example, or it may be provided on tangible media, such as optical, magnetic or electronic memory media. Alternatively, some or all of the functions of processor 40 may be carried out by dedicated or programmable digital hardware components, or using a combination of hardware and software elements.

An input/output (I/O) interface 42 enables console 24 to interact with probe 22. Based on the signals received from probe 22 (via interface 42 and other components of system 20), processor 40 drives a display 44 to present operator 28 with a map 46 of cardiac electrophysiological activity, as well as providing visual feedback regarding the position of distal end 31 in the patient's body, as well as status information and guidance regarding the procedure that is in progress.

Alternatively or additionally, system 20 may comprise an automated mechanism (not shown) for maneuvering and operating probe 22 within the body of patient 30. Such mechanisms are typically capable of controlling both the longitudinal motion (advance/retract) of probe 22 and transverse motion (deflection/steering) of central shaft 34 and arms 32. In such embodiments, processor 40 generates a control input for controlling the motion of probe 22 based on the signals provided by the magnetic field transducer in the probe. These signals are indicative of both the position of central shaft 34, and of force exerted on the central shaft (i.e., via arms 32), as explained further hereinbelow.

Figure 2:
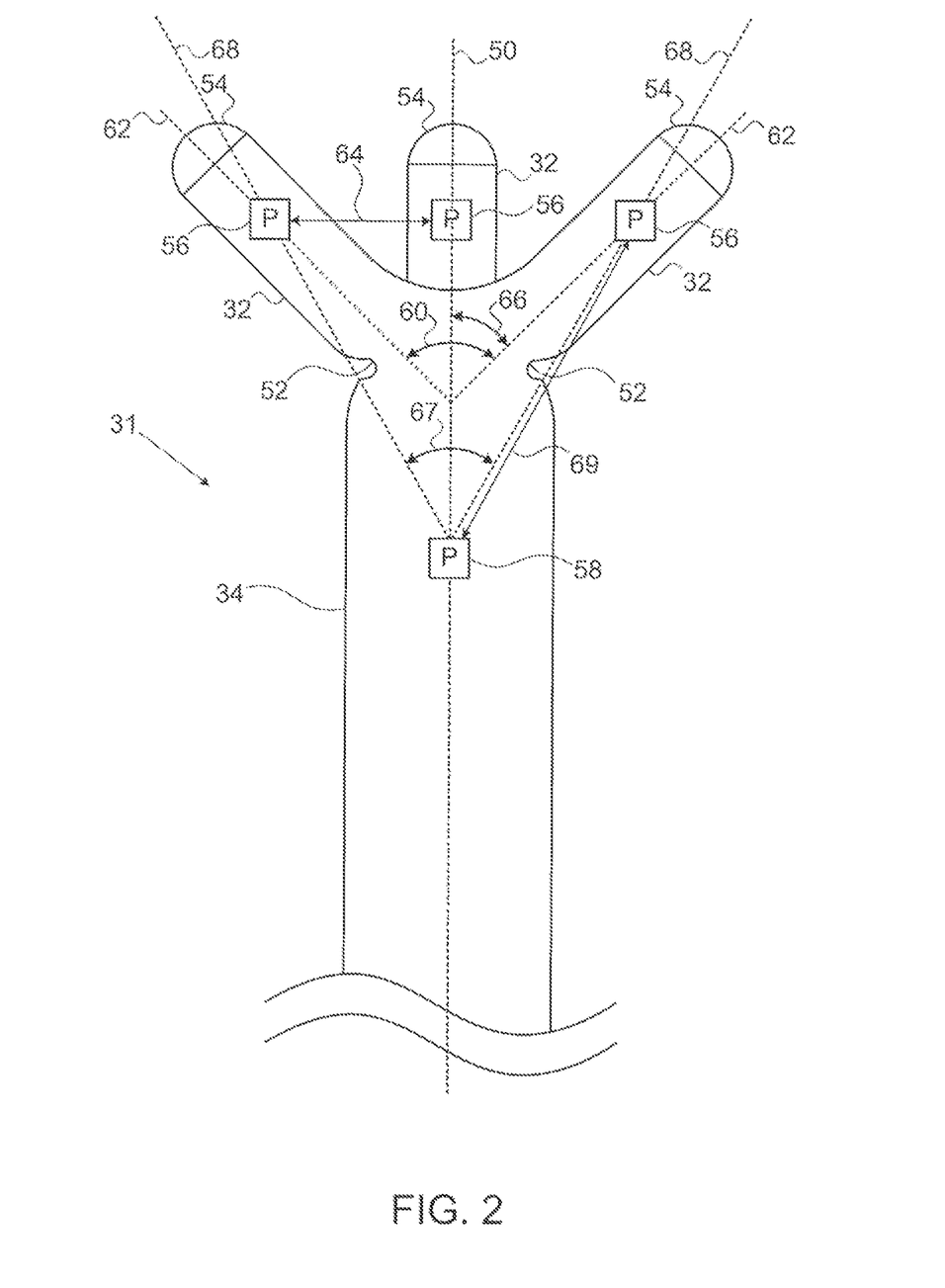
FIG. 2 is a schematic side view showing details of the distal portion of a multi-arm catheter, in accordance with an embodiment of the present invention.

FIG. 2 is a schematic side view of distal end 31 of multi-arm probe 22, in accordance with an embodiment of the present invention. Specifically, FIG. 2 shows functional elements of central shaft 34 and arms 32. Distal end 31 comprises a tuft of three arms 32 extending diagonally outward from central shaft 34. In the present example, arms 32 are substantially symmetrically arranged about a longitudinal axis of central shaft 34, although any other suitable arm configuration can also be used. FIG. 2 illustrates the arms substantially mutually spaced 120° apart about axis 50. A radial dimple 52 is formed at a juncture between central shaft 34 and each of arms 32, to enable the arms to bend backwards when pressing against a surface, such as the wall of heart 26.

Each of the arms comprises an electrode 54, which comes to contact with the heart tissue and senses electrical signals in the tissue. Electrode 54 may comprise, for example, a monopolar electrode or a bipolar electrode useful for determining local electrical activity (e.g., local activation time), and is typically made of a metallic material, such as a platinum/iridium alloy or another suitable material. Alternatively, multiple electrodes (not shown) along the length of each arm may be used for this purpose.

Each of the arms also comprises a position transducer 56, which generates a signal to console 24 that is indicative of the position coordinates of its respective arm 32. An additional position transducer 58 is fitted in central shaft 34 and generates a signal to console 24 that is indicative of the position coordinates of the central shaft. Each of position transducers 56 and 58 may comprise one or more miniature coils, and typically comprises multiple coils oriented along different axes. Alternatively, position transducers 56 and 58 may comprise either another type of magnetic transducer, an electrode which serves as a position transducer, or position transducers of other types, such as impedance-based or ultrasonic position transducers. Although FIG. 2 shows a probe with a single position transducer in each of the arms, embodiments of the present invention may utilize probes with more than one position transducer in any of the arms. When distal end 31 is pressed against body tissue during a medical procedure, processor 40 of console 24 uses the signals received from position transducers 56, and sometimes transducer 58, to calculate the positions of the transducers.

In an alternative embodiment, the roles of position transducers 56, 58 and magnetic field generators 38 may be reversed. In other words, driver circuit 36 may drive magnetic field generators in position transducers 56 and 58, so as to generate magnetic fields. Coils 38 may be configured to sense the fields and generate signals indicative of the amplitudes of the components of these magnetic fields. In this embodiment, processor 40 receives and processes the signals from coils 38 in order to determine the position coordinates of central shaft 34 and arms 32 within heart 26.

When pressing against a body cavity wall, the displacement of arms 32, either relative to each other and/or relative to central shaft 34, gives a measure of the deformation of each of the arms. Based on the measurements received from position transducers 56 (and in some embodiments also transducer 58), processor 40 can calculate the pressure applied by arms 32 against the wall of heart 26. Thus, the combination of field generators 38 with position transducers 56 and 58 serves as a pressure sensing system. This pressure sensing system reads the pressure correctly regardless of whether the pressure is exerted on arms 32 head-on or at an angle.

In the present context, the term "estimating contact pressure" refers both to quantitative pressure measurement and to verification of physical contact. In other words, processor 40 may estimate a numerical magnitude of the pressure exerted by the arms, or verify whether or not the arms come to physical contact with the heart surface. In the latter case, processor 40 produces binary indications that indicate whether or not the arms are in physical contact with the surface.

Although FIGS. 1 and 2 show a particular system configuration, other system configurations can also be employed to implement embodiments of the present invention, and are thus considered to be within the spirit and scope of this invention. For example, the methods described hereinbelow may be applied using position transducers of other types, such as impedance-based or ultrasonic position transducers. The term "position transducer" as used herein refers to an element mounted on probe 22 which causes console 24 to receive signals indicative of the coordinates of the element. The position transducer may thus comprise a receiver on the probe, which generates a position signal to the control unit based on energy received by the transducer; or it may comprise a transmitter, emitting energy that is sensed by a receiver external to the probe. In some embodiments, some of the disclosed techniques can be used with a probe having only a single arm that is fitted with a position transducer. Furthermore, the methods described hereinbelow may similarly be applied in mapping and measurement applications using not only catheters, but also probes of other types, both in the heart and in other body organs and regions.

Contact Pressure Estimation Using Arm Position Measurements

As discussed supra, embodiments of the present invention provide methods and systems for measuring the contact pressure between distal end 31 and the intra-body tissue. In some embodiments, processor 40 processes signals from position transducers 56 in order to determine the position coordinates of arms 32, typically including both location and orientation coordinates. In some embodiments, processor 40 may use the collected measurements to calculate one or more angles between arms 32. With reference to FIG. 2, processor 40 may calculate one or more angles 60 between respective pairs of longitudinal axes 62 of arms 32. Alternatively or additionally, processor 40 may calculate one or more distances 64 between pairs of position sensors 56.

In alternative embodiments, processor 40 processes signals received from position transducer 58, as well, in order to determine the position coordinates of central shaft 34 and arms 32. Processor 40 may use the collected measurements to calculate an angle 66 between longitudinal axis 50 of shaft 34 and longitudinal axis 62 of one of arms 32. Such a calculation can be performed for one or more of position transducers 56. In another embodiment, processor 40 estimates the curvature of a given arm, or of multiple arms, based on the signals received from position transducers 56 and 58. The estimated curvature can also be used as an indicator of contact pressure or physical contact. In an example embodiment, processor 40 senses that a give arm makes physical contact with the tissue by detecting a change in the curvature of the arm.

In further alternative embodiments, processor 40 may use the collected measurements to calculate an angle 67 between a pair of arcs 68, where each arc 68 traverses position transducer 58 and one of position sensors 56. Alternatively or additionally, processor 40 may calculate a respective distance 69 between position sensor 58 and a given position sensor 56. Again, this calculation can be performed for one or more of position transducers 56.

To determine the exerted pressure, processor 40 may use coefficients (typically pre-calculated during a calibration procedure) to estimate the pressure arms 32 are exerting on the intra-body tissue in question based on the calculated distances and/or angles.

In some embodiments, display 44 may present map 46 as a component of a novel user interface. For example, processor 40 may modify the way in which electrodes 54 in arms 32 are displayed on display 44, based on the estimated contact pressure. For example, if the contact pressure is within a predefined range that is regarded acceptable, the electrodes can be displayed using a certain color, icon or other graphical feature. If the contact pressure is outside the desired range, a different graphical feature will be used to display the electrodes. In an embodiment, processor 40 may refrain from displaying the electrodes if the contact pressure is out of range.

In some embodiments, processor 40 may enable sensing of electrical signals by electrodes 54 only when there is sufficient contact pressure against the wall of heart 26 (so that the potential measurement is likely to be valid).

In some embodiments, processor 40 may estimate the contact pressure applied by distal end 31 as a whole. In alternative embodiments, processor 40 may estimate and output the individual contact pressure exerted by each individual arm 32. For example, the processor may decide how to display a given arm 32 on display 44, or whether to enable sensing by the respective electrode 54, based on the specific pressure exerted by that individual arm.

Figure 3:
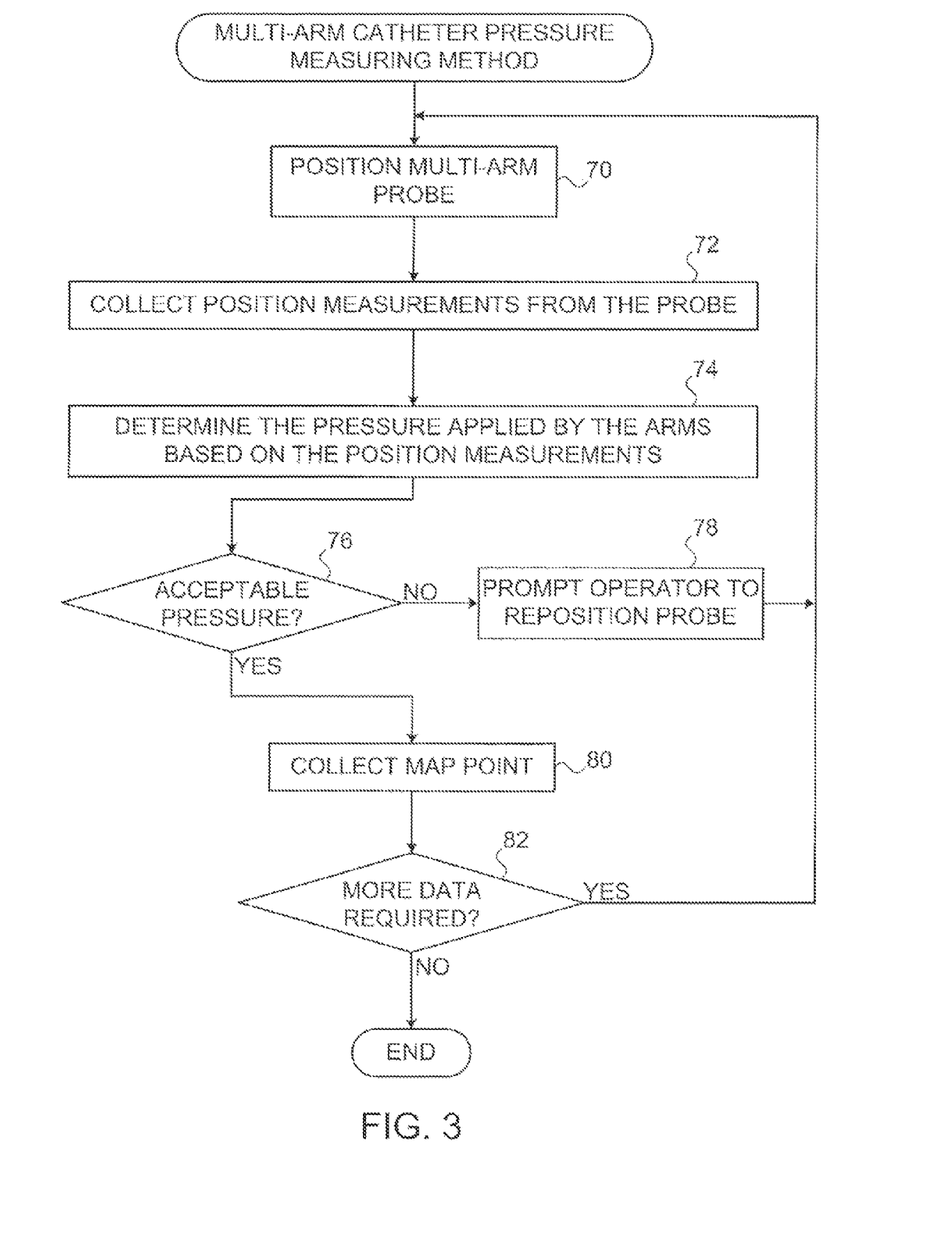
FIG. 3 is a flow diagram that schematically illustrates a method of measuring pressure exerted by a multi-arm catheter on an intra-body surface, in accordance with an embodiment of the present invention.

FIG. 3 is a flow diagram that schematically illustrates a method of measuring the pressure exerted by probe 22 on an intra-body surface, in accordance with an embodiment of the present invention. After operator 28 positions probe 22 (step 70) in heart 26, processor 40 processes the signals generated by position transducers 56 and 58 (step 72) and estimates the pressure exerted by arms 32 on endocardial tissue of heart 26 based on the signals (step 74). As discussed supra, processor 40 may derive the pressure based on parameters such as distances 64 and 69 or angles 60, 66 and 67. Processor 40 may use either a single parameter, or a combination of these or other parameters. Low pressure indicates that there may be inadequate contact between electrodes 54 and the endocardial tissue. High pressure may indicate that the electrodes are pressing too hard against the endocardial tissue.

Processor 40 checks whether the pressure measured at step 74 above is within a pre-specified acceptable range (step 76). If the contact quality is not within the specified range, console 24 may output an indication to display 44 of the pressure measured, and may issue an alert if the pressure is too low or too high, thereby prompting operator 28 to reposition probe 22 (step 78). The method then returns to step 70. Alternatively or additionally, the pressure indication may be used in closed-loop control of an automated mechanism for maneuvering and operating probe 22, as described hereinabove, to ensure that the mechanism causes arms 32 to engage the endocardium in the proper location, and with the appropriate pressure against the tissue.

If the contact pressure is within the specified range (step 76), processor 40 operates electrodes 54, e.g., collects map points (step 80), and updates map 46. Finally, if operator 28 desires to collect additional mapping data (step 82), then the method returns to step 70 until the map is completed.

Although the operation of position transducers 56 and 58 is described above in the context of using a catheter for acquisition of electrophysiological mapping data, the principles of the present invention may similarly be applied in other therapeutic and diagnostic applications that use invasive probes, both in heart 26 and in other organs of the body. For example, the devices and techniques that are implemented in system 20 may be applied, mutatis mutandis, in gated mapping of other physiological parameters, such as temperature or chemical activity, both in the heart and in other organs. Alternatively, system 20 may operate various other kinds of electrodes when the contact pressure is within range, e.g., apply ablation.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

The invention claimed is:

1. A method for operating a medical probe having a central shaft, comprising: pressing one or more of a plurality of arms each having a distal end that extends outward from the central shaft with each arm having a position transducer coupled thereto, against an intra-body surface, so as to cause the arms to exert pressure on the surface and bend with respect to the central shaft in response to the pressure; measuring positions of the respective position transducers coupled to the arms using a processor; and estimating, using the processor, the pressure exerted by at least one arm on the intra-body surface in response to the measured positions by calculating at least one angle between the central shaft and the at least one arm, and estimating, using the processor, the pressure responsively to the at least one angle.

2. The method according to claim 1, wherein the medical probe comprises a catheter.

3. The method according to claim 1, wherein measuring the positions comprises applying one or more magnetic fields in a vicinity of the probe, receiving from the position transducers respective signals, which are generated by the position transducers responsively to the magnetic fields and are indicative of the respective positions of the position transducers, and calculating the positions based on the received signals.

4. The method according to claim 1, wherein estimating the pressure comprises calculating at least one angle between at least one respective pair of the arms, and estimating the pressure responsively to the angle.

5. The method according to claim 1, wherein estimating the pressure comprises applying to the measured positions a pre-calibrated relation between the pressure and the positions.

6. The method according to claim 1, wherein measuring the positions comprises measuring a position of an additional position transducer that is coupled to the central shaft, and wherein estimating the pressure comprises assessing the pressure responsively to the measured position of the additional position transducer.

7. The method according to claim 6, wherein estimating the pressure comprises calculating at least one distance between the additional position transducer and a respective at least one of the position transducers, and estimating the pressure responsively to the distance.

8. The method according to claim 6, wherein estimating the pressure comprises calculating at least one angle between the central shaft and a respective at least one of the arms, and estimating the pressure responsively to the angle.

9. The method according to claim 1, and comprising displaying an image of the arms and the surface to an operator, and selecting a graphical feature using which the arms are presented in the image responsively to the estimated pressure.

10. The method according to claim 1, and comprising selectively enabling sensing of signals by one or more electrodes coupled to at least one of the arms responsively to the estimated pressure.

11. A medical apparatus comprising: a central shaft having a distal end; a plurality of arms each having a distal end that extends outward from the central shaft with each arm having a position transducer coupled thereto, the arms configured to press against an intra-body surface, so as to cause the arms to exert pressure on the surface and bend with respect to the central shaft in response to the pressure; a processor configured to measure positions of the respective position transducers coupled to the arms and estimate the pressure exerted by at least one arm on the intra-body surface by calculating at least one angle between the central shaft and the at least one arm, and to estimate the pressure exerted by the at least one arm on the intra-body surface responsively to the at least one angle.

12. The apparatus according to claim 11, wherein the medical probe comprises a catheter.

13. The apparatus according to claim 11, wherein the processor is configured to cause one or more field generators to apply one or more magnetic fields in a vicinity of the probe, to receive from the position transducers respective signals, which are generated by the position transducers responsively to the magnetic fields and are indicative of the respective positions of the position transducers, and to calculate the positions based on the received signals.

14. The apparatus according to claim 11, wherein the processor is configured to calculate at least one angle between at least one respective pair of the arms, and to estimate the pressure responsively to said at least one angle.

15. The apparatus according to claim 11, wherein the processor is configured to estimate the pressure by applying to the measured positions a pre-calibrated relation between the pressure and the positions.

16. The apparatus according to claim 11, and comprising an additional position transducer coupled to the central shaft, wherein the processor is configured to measure a position of the additional position transducer, and to estimate the pressure responsively to the measured position of the additional position transducer.

17. The apparatus according to claim 11, wherein the processor is configured to calculate at least one distance between the additional position transducer and a respective at least one of the position transducers, and to estimate the pressure responsively to the distance.

18. The apparatus according to claim 11, wherein the processor is configured to calculate at least one angle between the central shaft and a respective at least one of the arms, and to estimate the pressure responsively to the angle.

19. The apparatus according to claim 11, wherein the processor is coupled to display an image of the arms and the surface to an operator, and to select a graphical feature using which the arms are presented in the image responsively to the estimated pressure.

20. The apparatus according to claim 11, wherein the probe comprises one or more electrodes coupled to at least one of the arms, and wherein the processor is configured to selectively enable sensing of signals by the electrodes responsively to the estimated pressure.

* * * * *